(12) United States Patent
LaTorre et al.

(10) Patent No.: US 12,161,852 B2
(45) Date of Patent: Dec. 10, 2024

(54) MEDICAL WASTE DISPOSAL AND CONTAINER WASHING SYSTEM

(71) Applicant: Stericycle, Inc, Bannockburn, IL (US)

(72) Inventors: Matthew S. LaTorre, Smithtown, NY (US); Paul Joseph Gulczynski, Randolph, MA (US); Keith William Hiss, Baldwin, MD (US); Jeremy Ryan Salkin, Chester, MD (US); Franklin John Schaefer, Jr., Fallston, MD (US)

(73) Assignee: Stericycle, Inc, Bannockburn, IL (US)

( * ) Notice: Subject to any disclaimer, the term of this patent is extended or adjusted under 35 U.S.C. 154(b) by 268 days.

(21) Appl. No.: 17/744,427

(22) Filed: May 13, 2022

(65) Prior Publication Data

US 2023/0166049 A1 Jun. 1, 2023

Related U.S. Application Data

(62) Division of application No. 17/539,663, filed on Dec. 1, 2021, now Pat. No. 11,357,928.

(51) Int. Cl.
*A61M 5/32* (2006.01)
*A61L 2/26* (2006.01)
(Continued)

(52) U.S. Cl.
CPC ............. *A61M 5/3278* (2013.01); *A61L 2/26* (2013.01); *B25J 9/0093* (2013.01); *B65G 17/30* (2013.01);
(Continued)

(58) Field of Classification Search
CPC ......... A61M 5/3278; A61M 2005/3228; A61L 2/26; A61L 2202/17; A61L 2202/24; B25J 9/0093; B65G 17/30
See application file for complete search history.

(56) References Cited

U.S. PATENT DOCUMENTS 5,273,221 A 12/1993 McCarthy
5,368,652 A 11/1994 Mullinax
(Continued)

FOREIGN PATENT DOCUMENTS

CA 2630354 C 2/2017
CN 112871958 A 6/2021
(Continued)

OTHER PUBLICATIONS

Better Engineering Mfg. Inc., "Tote Washers", website: https://www.betterengineering.com/tote-washers-bin-washers/, accessed on or about Aug. 9, 2021 (1 Page).
(Continued)

*Primary Examiner* — Sean E Conley
(74) *Attorney, Agent, or Firm* — Michael Best & Friedrich LLP

(57) ABSTRACT

A medical waste disposal and container washing system includes loading and unloading stations, the loading station configured for placing a medical waste container on a conveyor system. An inversion station is located downstream along the conveyor system, operable to reorient the container from a first orientation in which medical waste is retained to a second orientation in which the medical waste is discharged from the medical waste container by gravity as the medical waste container is moved within the inversion station. A first wash station along the conveyor system washes an interior of the container that has been reoriented. A second wash station is located downstream along the conveyor system.

15 Claims, 7 Drawing Sheets

(51) Int. Cl.
*B25J 9/00* (2006.01)
*B65G 17/30* (2006.01)

(52) U.S. Cl.
CPC ....... *A61L 2202/17* (2013.01); *A61L 2202/24* (2013.01); *A61M 2005/3282* (2013.01)

(56) References Cited

U.S. PATENT DOCUMENTS

| | | |
|---|---|---|
| 5,470,546 A | 11/1995 | Hall |
| 6,348,174 B1 | 2/2002 | Hall |
| 6,702,099 B2 | 3/2004 | Ortaguro et al. |
| 7,325,667 B1 | 2/2008 | Damick et al. |
| 7,749,330 B2 | 7/2010 | Lin et al. |
| 8,585,832 B2 | 11/2013 | Lin et al. |
| 9,707,595 B2 | 7/2017 | Ripley |
| 10,858,205 B2 | 12/2020 | Oriols Gaja et al. |
| 2008/0105515 A1 | 5/2008 | Damick et al. |
| 2008/0240979 A1 | 10/2008 | Lin et al. |
| 2009/0314692 A1 | 12/2009 | Bennett et al. |
| 2018/0111176 A1 | 4/2018 | Miller et al. |
| 2021/0259509 A1 | 8/2021 | Sperry |

FOREIGN PATENT DOCUMENTS

| | | |
|---|---|---|
| JP | H05185048 A | 7/1993 |
| JP | 2002136938 A | 5/2002 |
| JP | 2002263603 A | 9/2002 |
| WO | WO2014128481 A1 | 8/2014 |
| WO | WO2019207200 A1 | 10/2019 |
| WO | WO2020193397 A1 | 1/2020 |

OTHER PUBLICATIONS

Better Engineering Mfg. Inc., "Ultima-San Jet Washers", Product Brochure, website: www.betterengineering.com, accessed on or about Feb. 2021 (9 Pages).

GR-X Manufacturing, "Automatic Can Depalletizer with Slide grip Lowerator", You Tube Video: https://www.youtube.com/watch?v=e1AWAF0cobo, Apr. 1, 2019 (2 screenshots).

United Kingdom Intellectual Property Office. Examination Report for Application No. GB2215963.6, dated Sep. 19, 2024 (5 pages).

MEDICAL WASTE DISPOSAL AND CONTAINER WASHING SYSTEM

CROSS-REFERENCE TO RELATED APPLICATIONS

This application is a divisional of U.S. patent application Ser. No. 17/539,663, filed Dec. 1, 2021, the entire contents of which are incorporated by reference herein.

BACKGROUND

The invention relates to systems for emptying the contents of medical waste (e.g., sharps) containers as well as washing the containers. Such systems are automated in certain aspects to minimize the need for personnel to come into contact with the waste contents. Automation has included the use of fixed-base robotic arms to empty the containers. Empty containers may then be processed through a conveyorized tunnel washer. The tunnel washer may be designed to meet FDA certification for medical devices.

SUMMARY

In one aspect, the invention provides a method of operating a medical waste disposal and container washing system. A medical waste container is loaded to the medical waste disposal and container washing system, the medical waste container including medical waste enclosed in the container by a lid. The lid is removed from the medical waste container with a robotic tool following the loading of the medical waste container to the medical waste disposal and container washing system. The medical waste container is transported via a conveyor system to an inversion station. The medical waste container is reoriented at the inversion station from a first orientation in which the medical waste is retained within the medical waste container as the medical waste container is moved within the inversion station to a second orientation in which the medical waste is discharged from the medical waste container by gravity as the medical waste container is moved within the inversion station. The medical waste container is transported in the second orientation through a first wash station located along the conveyor system to wash an interior of the medical waste container that has been reoriented to the second orientation. The medical waste container is transported through a second wash station located along the conveyor system and downstream from the first wash station. The medical waste is collected and removed from the medical waste disposal and container washing system. Following the lid removal, the conveyor system moves the medical waste container continuously through the inversion station, from the inversion station to the first wash station, through the first wash station, from the first wash station to the second wash station, and through the second wash station without stopping.

In another aspect, the invention provides a medical waste disposal and container washing system. The system includes a loading station located at an upstream end of the medical waste disposal and container washing system, wherein the loading station is configured for placing a medical waste container on a conveyor system. An inversion station is located along the conveyor system downstream from the loading station and operable to reorient the medical waste container from a first orientation in which medical waste is retained within the medical waste container as the medical waste container is moved within the inversion station to a second orientation in which the medical waste is discharged from the medical waste container by gravity as the medical waste container is moved within the inversion station. A first wash station is located along the conveyor system, the first wash station positioned and configured to wash an interior of the medical waste container that has been reoriented to the second orientation. A second wash station is located along the conveyor system and downstream from the first wash station. An unloading station is downstream from the second wash station and configured for removal of the medical waste container from the conveyor system.

DETAILED DESCRIPTION

Before any embodiments of the present invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Sharp medical devices are used on patients in invasive procedures, necessitating strict requirements for post-use handling and disposal. Used medical devices are unclean, often having been in contact with blood or other bodily fluids of a patient, but are still sharp. Indeed, many of these medical devices have a point or edge sharp enough to penetrate containers designated for common waste. Single-use medical devices are thus commonly disposed after use in a "sharps" container. Sharps containers are well known to those who work in medical care facilities and are intended to be used to collect potentially dangerous, used sharp medical devices that are capable of cutting or penetrating skin or penetrating a conventional waste package container. Sharps containers may contain used syringes, needles, and broken glass. These containers are periodically picked up from a medical care facility by a regulated waste collector and transported to an off-site disposal location. In some cases, the medical care facility may purchase sharps containers outright and, when filled, contract a service to remove the permanently sealed containers, which are then completely destroyed (e.g., via comminution and/or incineration) along with the contents thereof. In other cases, medical care facilities rent reusable sharps containers. When these containers are filled, they are transported to a disposal site where they are opened, emptied, and then cleaned and disinfected before being returned to the same or other medical care facility for reuse.

Figure 1:
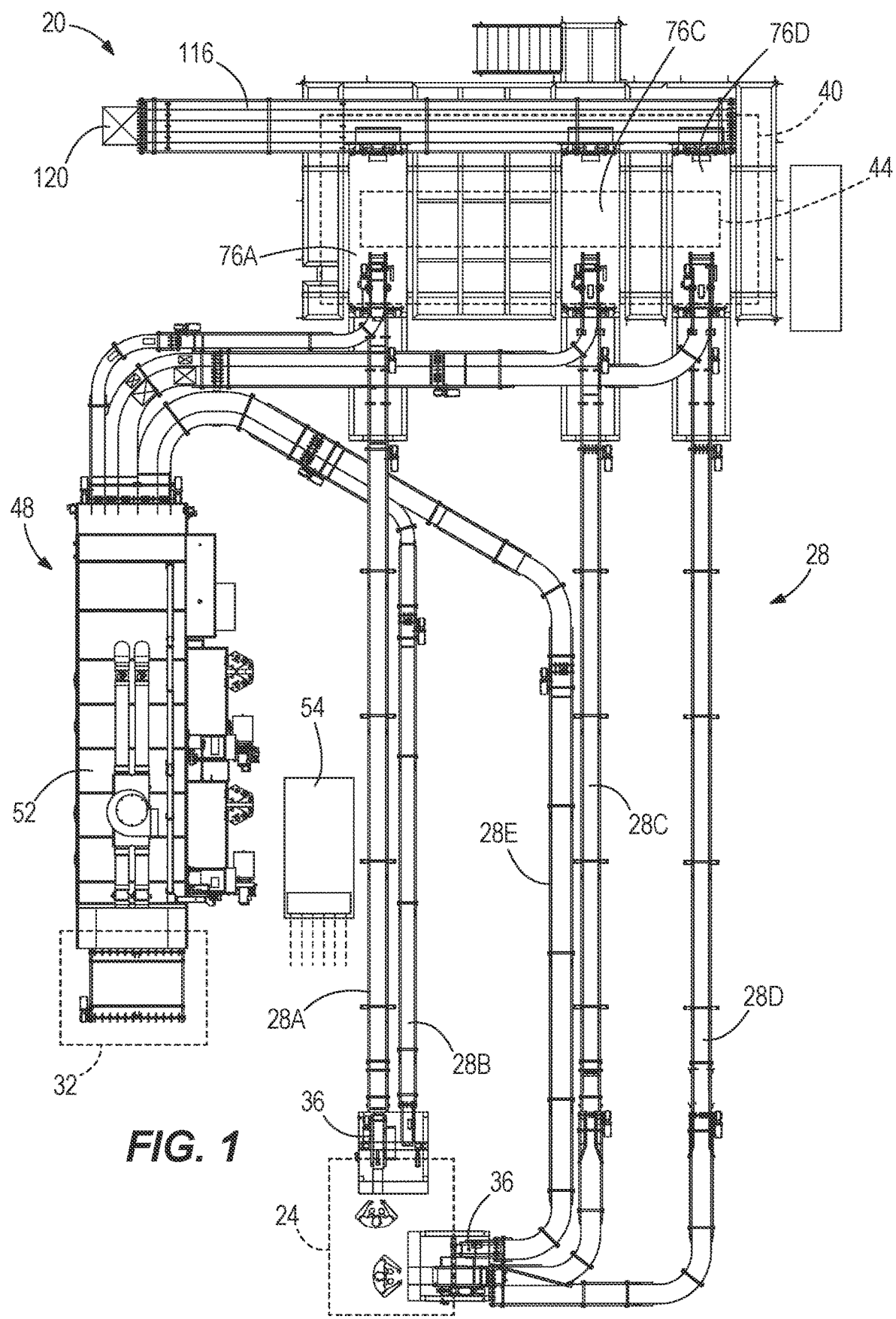
FIG. 1 is a top plan view of a medical waste disposal and container washing system according to one embodiment of the present disclosure.

FIG. 1 illustrates a medical waste disposal and container washing system 20, referred to hereinafter simply as the system 20. The system 20 is configured to receive and process various reusable sharps containers holding disposable medical waste, e.g. single-use medical devices (SUDs) or other types of medical waste. For ease of reference we will refer to all such medical waste containers as "sharps containers," although the containers may be suitable to hold other types of medical waste. The containers themselves may be classified as reprocessable medical devices that can legally be reused only if reprocessed consistent with FDA regulations. In particular, FDA approval must be obtained through an application and certification procedure for the party intending to reuse sharps containers.

The system 20 incorporates numerous advantageous features, which in some constructions can be used in isolation or in separate combinations, although the below description focuses on the illustrated embodiment. For example, the system 20 as described below is configured to accept and process multiple (e.g., two, three, four, five or more) different sizes of sharps containers. These various sharps containers may all have a similar shape and vary only in scaling of the dimensions to achieve different volumetric capacities. In other constructions, some or all of the various containers processed through the system 20 may have dissimilar shapes and the same or different volumetric capacities. The system 20 is also configured to provide continuous flow operation as will be appreciated from the following description. In some aspects, the system 20 provides multiple parallel conveyor lanes that operate concurrently and feed into the same enclosed washing device, or "tunnel washer." Containers may have their lids removed after loading to the system 20, and separate conveyor lanes may be provided for the lids and the lid-less containers. The containers are emptied during transport by the conveyor system. Upon emptying, the containers are pre-washed during transport by the conveyor system to the washer. The pre-wash can be incorporated into the FDA certification, and may allow for faster processing speeds through the tunnel washer, ultimately yielding increased throughput of the system 20.

The system 20 includes a loading station 24 where filled, closed sharps containers are brought for loading onto a conveyor system 28. The loading station 24 defines the upstream end of the system 20. The system 20 further includes an unloading station 32 where clean, empty containers and separated lids are unloaded from the conveyor system 28. The unloading station 32 defines the downstream end of the system 20. The conveyor system 28 can define a conveyor path or paths with multiple turns or curves in plan view between the upstream and downstream ends. In some constructions, the conveyor system 28 is shaped to position the unloading station 32 adjacent the loading station 24 for ease of transportation to and from the system 20, e.g., from and to a loading dock of the facility. As described below, the conveyor system 28 can be configured to receive containers at multiple points to supply multiple conveyor lanes. The loading station 24 can be considered to incorporate all container loading points to the conveyor system 28. Alternately, each loading point can be considered to constitute a discrete loading station.

Along the conveyor system 28 are located (in sequence with respect to a travel direction of the conveyor system): a lid removal station 36, an inversion station 40, a first wash station 44, and a second wash station 48. The lid removal station 36 may overlap the loading station 24 in plan view (FIG. 1). Similarly, the first wash station 44 may overlap the inversion station 40 in plan view. The first wash station 44 is referred to hereinafter as the "pre-wash" and is separate and spaced from the second wash station 48 or "main wash." The second wash station 48 can span a greater length of the conveyor system 28 than the pre-wash station 44. Likewise, residence time of containers through the second wash station 48 can be greater than residence time of containers through the pre-wash station 44 during operation of the system 20. The second wash station 48 can consist in some constructions of a commercially available conveyorized tunnel washer 52. The washer 52 can include multiple sequential stages or modules therein, such as wash, sanitize, rinse, and dry.

As one non-limiting example, the washer 52 can be a model C-60/S4/S4 from Better Engineering Mfg, Inc. of Joppa, MD The washer 52 can have a 60-inch conveyor width, although the conveyor width can be scaled up or down in other constructions depending upon the size of expected containers and/or the number of conveyor lanes that feed into the washer 52. As will be more fully appreciated from the following description, the pre-wash station 44 provides a liquid spray into inverted sharps containers. In some constructions, the sharps containers remain inverted when conveyed into and through the washer 52.

The illustrated conveyor system 28 includes multiple conveyor lanes. Each conveyor lane may be provided as one or more conveyors or conveyor segments of various types (belt, chain, etc.) that establish a designated path from the loading station 24 to the unloading station 32. The individual conveyors providing the conveyor lanes can be under control (e.g., start/stop timing, running speed) of one or more electronic controllers 54. The conveyor lanes can include one or more lanes for containers and one or more separate lanes for container lids. As shown, the conveyor lanes of the conveyor system 28 include: a first conveyor lane 28A configured to receive a first container, a second conveyor lane 28B configured to receive a lid removed from the first container, a third conveyor lane 28C configured to receive a second container, a fourth conveyor lane 28D configured to receive a third container, and a fifth conveyor lane 28E configured to receive lids removed from the second and third containers.

The first, second, and third containers are different from each other in volumetric capacity and differ in at least one exterior dimension in a three-dimensional Cartesian system. In addition, one or more of the container conveyor lanes 28A, 28C, 28D can receive multiple sizes of containers, e.g., containers of different volumetric capacity having at least one common exterior dimension. In one non-limiting example, the first conveyor lane 28A handles 2-gallon and 3-gallon containers, the third conveyor lane 28C handles only 4-gallon containers, and the fourth conveyor lane 28D handles 8-gallon and 17-gallon containers. In such an example, the second conveyor lane 28B handles the lids of the 2-gallon and 3-gallon containers, and the fifth conveyor lane 28E handles the lids of the 4-gallon, 8-gallon, and 17-gallon containers. Alternate combinations are contemplated. For example, the 4-gallon containers may be grouped on a conveyor lane with the 8-gallon and/or 17-gallon containers. The system 20 may use all or less than all of the available lanes through the washer 52. The lid conveyor lane(s) 28B, 28E extend from the loading station 24 to the washer 52, bypassing the inversion station 40. The lid conveyor lane(s) 28B, 28E can also bypass the pre-wash 44 station.

Despite the system 20 being operable with a number of unique containers and lids, the description that follows along with the related drawings will refer to any/all containers with the reference character "C" and to any/all lids as "L" (except where explicitly noted otherwise). In instances where the container is shown with the lid attached, the reference character "CL" is used.

Figure 2:
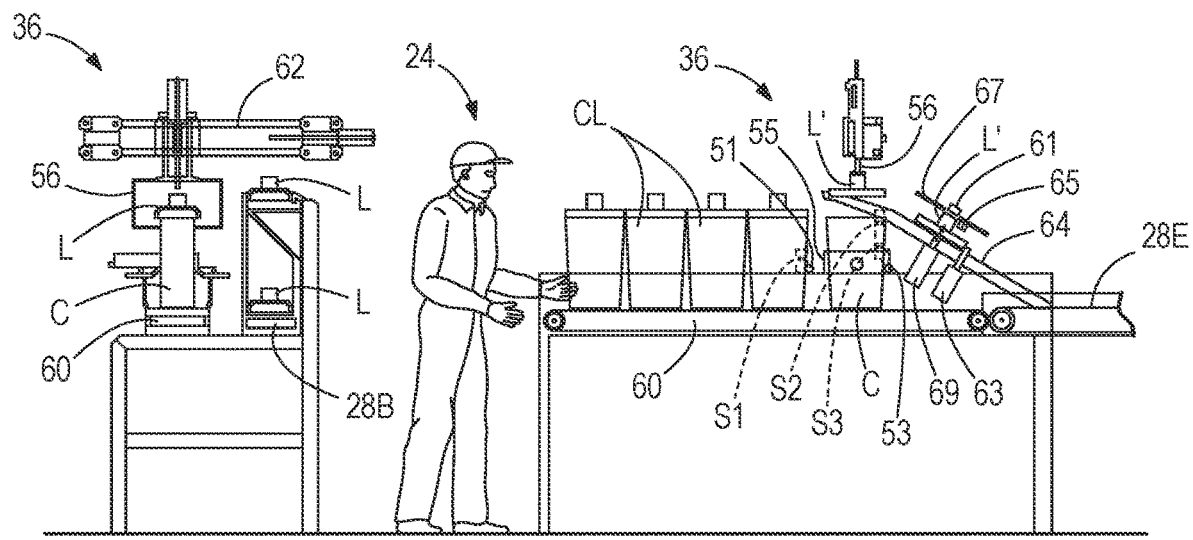
FIG. 2 is a side elevation view of an exemplary loading station of the medical waste disposal and container washing system of FIG. 1, including a robotic lid removal tool. Portions of the system are removed to show a lid chute and lid conveyor lane.
Figure 3:
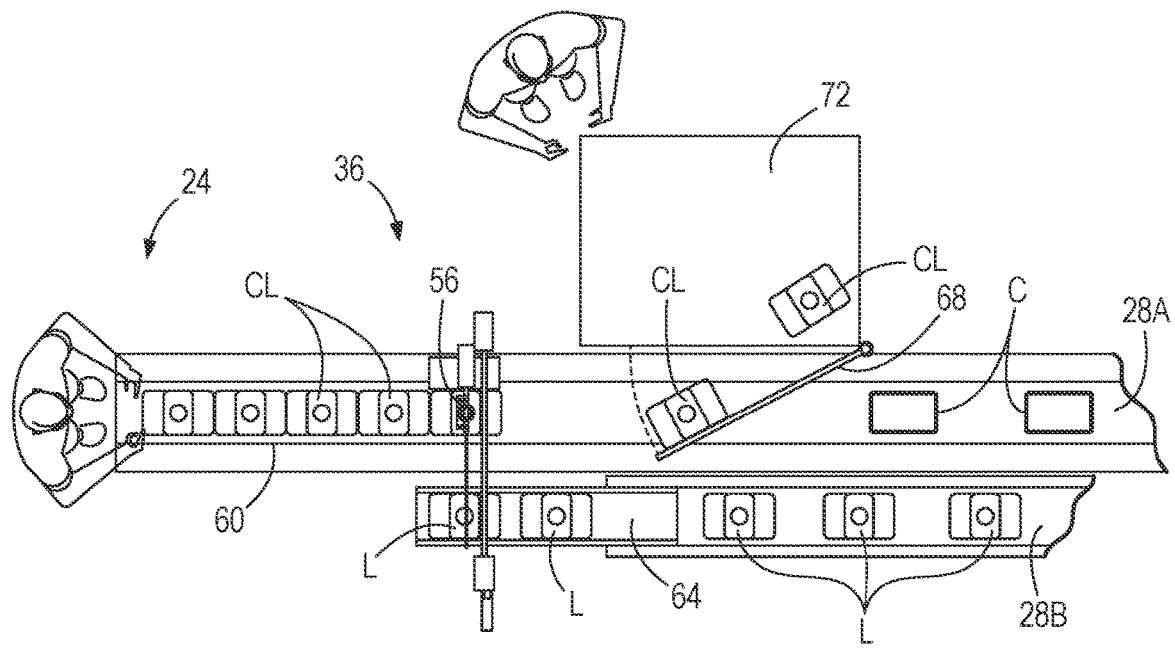
FIG. 3 is a top plan view of a portion of the loading station, including two conveyor lanes extending therefrom.

At the lid removal station 36, a robotic tool 56 is provided (e.g., suspended) above the initial portion of the conveyor system 28 at the loading station 24. FIGS. 2 and 3 show additional side elevation and plan views thereof. Although not illustrated, the lid removal station 36 may be enclosed around its perimeter by walls that inhibit human access during normal operation. One of these walls can include an opening large enough for entry of the incoming containers CL. The robotic tool 56 is operable to disengage and remove a lid L from a container C positioned in line with one of the container conveyor lanes 28A, 28C, 28D. The illustrated construction shows separate lid removal stations 36 with separate robotic tools 56—one for the containers entering the first conveyor lane 28A and another for the containers entering the third and fourth conveyor lanes 28C, 28D. Thus, the system 20 includes provisions for removing multiple lids L from multiple containers C concurrently. In some constructions, more than one robotic tool 56 is provided within one or both of the lid removal stations 36. For example, the lid removal station 36 at the bottom of the view of FIG. 1 can include two robotic tools 56, one of which is dedicated to a single container size (e.g., 4-gallon containers). Each robotic tool 56 operates to remove the container lid L while the closed container CL is positioned on an entry conveyor 60 of the conveyor system 28. The entry conveyor 60 can be aligned with the respective container conveyor lanes 28A, 28C and may be considered to form inlet portions of these respective container conveyor lanes 28A, 28C. At least one of the entry conveyors 60 supplies containers C to multiple container conveyor lanes (e.g., lanes 28C, 28D at the lid removal station illustrated at the bottom of FIG. 1 and at the right of FIG. 2).

In accordance with the following description, the container CL is held stationary on the entry conveyor 60 during lid removal. In other constructions, the robotic tool 56 can be configured to move along with the closed container CL on the conveyor system 28 while operating to separate the lid L from the container C. As shown on the right side of FIG. 2, a plurality of closed containers CL loaded to the entry conveyor 60 can be individually metered to the lid removal position by a metering stop 51 (e.g., an extendable rod of a pneumatic cylinder). The presence of a container CL at the metering stop 51 can be detected by a sensor S1 such as an optical sensor. When the lid removal position becomes vacant, a next-in-line closed container CL is moved into the lid removal position along the entry conveyor 60. The next-in-line closed container CL is advanced by retraction of the metering stop 51 and forward operation of the entry conveyor 60. The metering stop 51 then deploys again to stop the directly trailing closed container CL. The closed container CL advanced into the lid removal position can be stopped at the lid removal position by an additional stop 53 (e.g., an extendable rod of a pneumatic cylinder). A clamp 55 can also engage the container CL at the lid removal position (e.g., from the side). The closed container CL may remain gripped by the clamp 55 during manipulation of the robotic tool 56 to remove the lid L, which may include upward prying and/or lifting with respect to the container C. At the lid removal position, one or more additional sensors S2, S3 are operable to detect the container height so that a controller (e.g., the controller 54 or a local sub-controller) can provide positional instruction and control movement of the robotic tool 56 to the proper height for container lid removal. As illustrated, the system includes multiple sensors S2, S3 arranged at different vertical heights that are set in relation to expected heights of the incoming containers, thus enabling a simple determination. In other constructions, an alternate sensor arrangement can directly measure the container height, or a robotic tool-mounted proximity sensor may be provided to guide the robotic tool 56 to the lid to be removed. The sensors S2, S3 can be optical presence sensors in some constructions.

Once the lid L is removed, the robotic tool 56 can transport the lid in a direction toward one of the lid conveyor lanes 28B, 28E. This movement can include a lateral shift with respect to the direction of the entry conveyor 60. The robotic tool 56 can be suspended from an overhead gantry 62 for movement along the gantry to a lid release position. In some constructions, the robotic tool 56 can release the lid L onto an upper portion of a slide or chute 64 that extends down at an oblique angle to the respective lid conveyor lane 28B, 28E. Thus, the lids L slide along the chute 64 by gravity, while avoiding a vertical fall. The right side of FIG. 2 has conveyor lanes 28C, 28D removed to illustrate the chute 64 and the lid conveyor lane 28E.

In some constructions, some of the container lids L' may include removable caps 61 configured to be separable from the lid L'. The right side of FIG. 2 illustrates optional features of the lid removal station 36 to accommodate such lids L', and particularly the separation of the removable caps 61 from the lids L'. A stop 63 (e.g., an extendable rod of a pneumatic cylinder) on the chute 64 locates the lid L' and stops the lid L', defining a cap ejection position along the chute 64. The stop 63 may be configured to stop every passing lid in this position, regardless of whether or not it has a cap 61 to be ejected. A sensor 65 at the cap ejection position may detect the cap 61, either directly or otherwise identifying the style of lid L' having the cap 61. In other constructions, cap detection can be carried out upstream, and the stop 63 is configured to only stop the lids L' having the separate caps 61.

Above the chute 64 at the cap ejection position is a cover plate 67 covering at least a portion of the lid L' and having an aperture therein sized for passage of the cap 61. The cover plate 67 can vertically restrain the lid L' while a cap removal plunger 69 is engaged from the bottom of the chute 64 to press the cap 61 upward and detach it from the lid L'. Thus, the system allows the cap 61 to be removed prior to the lid L' being released onto a conveyor. Once ejected from the lid L', the cap 61 can be blocked by the cover plate 67 from dropping back onto the chute 64 and instead redirected into a collection bin alongside the lid removal station 36. A plurality of caps 61 can be collected and routed through the washer 52 while contained in the collection bin, which can be a permeable basket. Containers having the lids L' with removable caps 61 can be limited to only one of the lid removal stations 36. As such, the components described above for handling the lids L' and ejecting the caps 61 can be provided at only one of the lid removal stations 36. In other constructions, system flexibility is afforded by providing both lid removal stations 36 with the components required for handling the lids L' with removable caps 61.

FIG. 3 illustrates optional additional equipment that may be incorporated along one or more lanes of the conveyor system 28, for example, adjacent the loading station 24. A manually-operable or electronically-controlled diverter 68 can be movable between a first position that enables passage of a lid-less container C and a second position that diverts a closed container CL to a reject table 72. For example, a closed container CL that gets past the lid removal station 36 (e.g., due to a malfunction of the robotic tool 56) will be directed by the diverter 68 to the reject table 72 rather than being passed onward to the container conveyor lane 28A, since the container C cannot be cleaned until the lid L is removed. The rejected container CL can either be opened by alternate means (e.g., manually or via a handheld tool) and placed back onto the conveyor system 28, or reloaded to the lid removal station 36 for an additional attempt at lid removal by the robotic tool 56.

Figure 4:
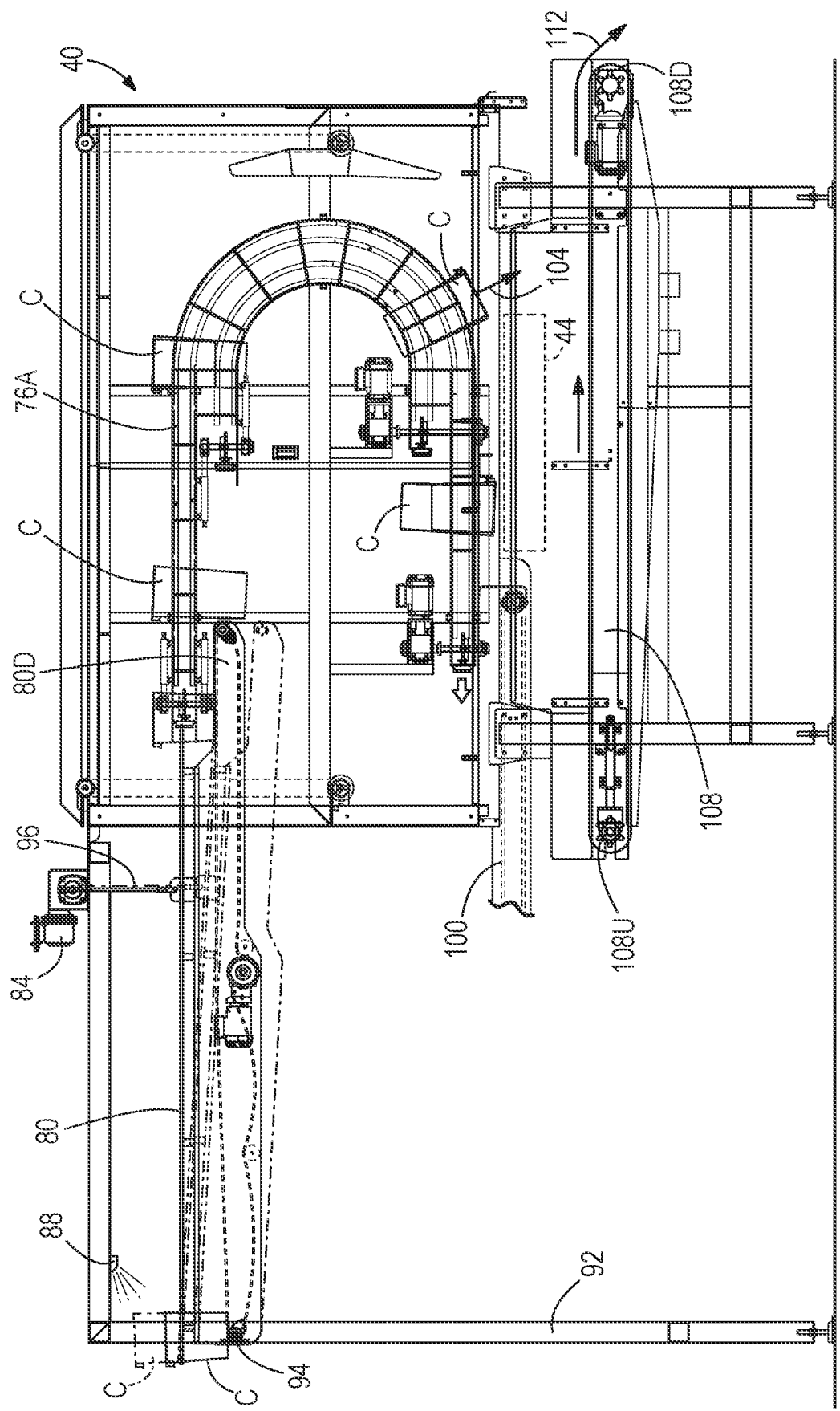
FIG. 4 is a side elevation view of an inversion station of the medical waste disposal and container washing system of FIG. 1, including a metering conveyor, a gripper inverter conveyor, a pre-wash station below a portion of the gripper inverter conveyor, and a dewatering conveyor below portions of the gripper inverter conveyor and the pre-wash station.
Figure 5:
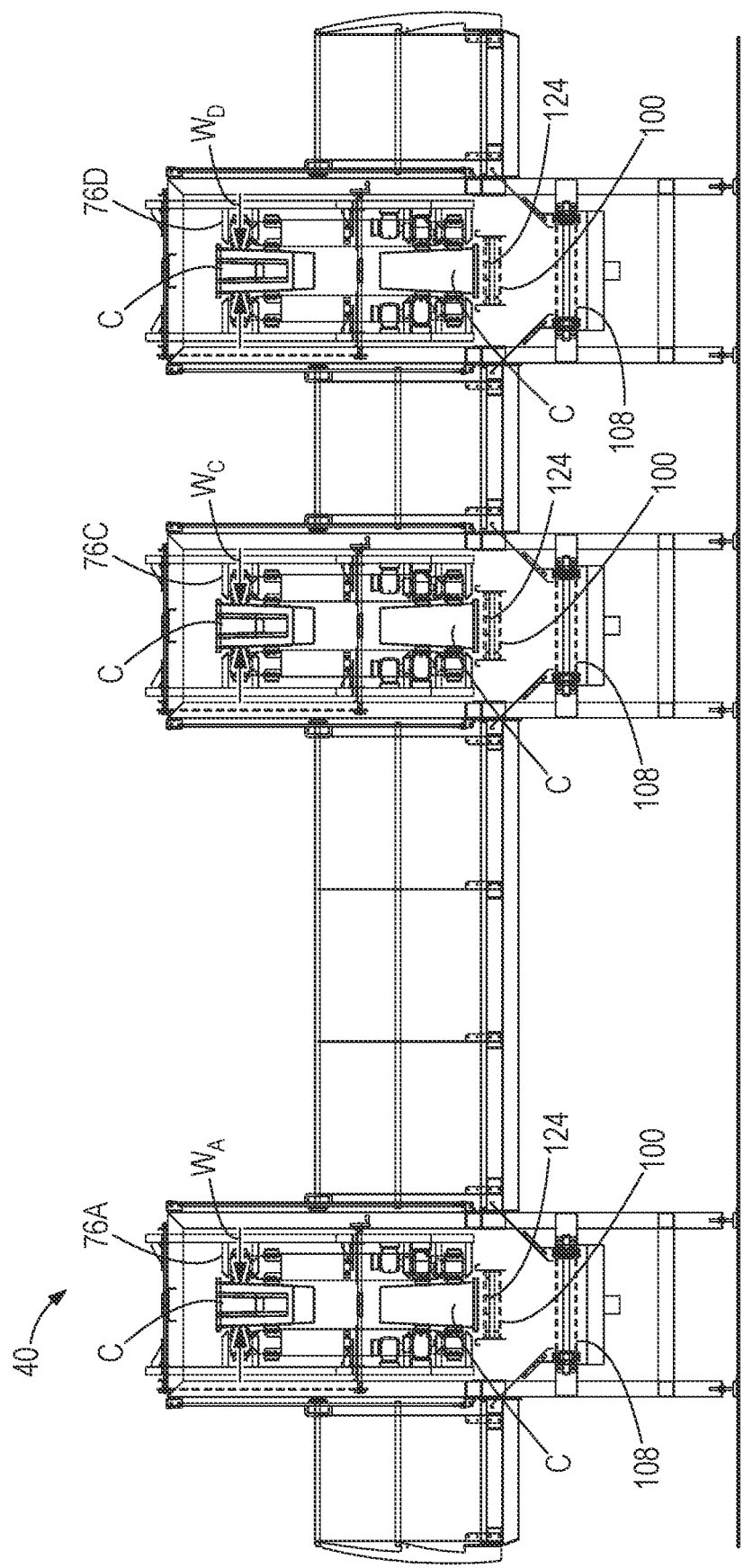
FIG. 5 is an end view of the inversion station of FIG. 4, including three parallel gripper inverter conveyors.

With the lids L removed from the containers C, the containers C are transported by the respective conveyor lanes 28A, 28C, 28D to the inversion station 40 as shown in FIG. 1. The inversion station 40, shown in more detail in FIGS. 4 and 5, is operable to reorient each sharps container C from a first orientation in which medical waste is retained within the container C as the medical waste container is moved within the inversion station 40 to a second orientation in which the medical waste is discharged from the container C by gravity as the container C is moved within the inversion station 40. The inversion station 40 includes at least one gripper inverter conveyor. In the illustrated construction where there are three container conveyor lanes 28A, 28C, 28D, the inversion station 40 includes three corresponding gripper inverter conveyors 76A, 76C, 76D. In other constructions, there may be two or more than three gripper inverter conveyors within the system 20.

The gripper inverter conveyors 76A, 76C, 76D are arranged within the illustrated system 20 to have respective lengths that extend in parallel directions. The individual gripper inverter conveyors 76A, 76C, 76D can differ from each other by having disparate track widths $W_A$, $W_C$, $W_D$, measured perpendicular to both a conveyor transport direction and a container height direction. The various track widths $W_A$, $W_C$, $W_D$ correspond to the widths of the containers C loaded to the respective conveyor lanes 28A, 28C, 28D such that each gripper inverter conveyor 76A, 76C, 76D is configured to grip the containers with opposed sets of movable grippers positioned on opposing lateral sides of the conveyor. The gripper inverter conveyors 76A, 76C, 76D can be constructed with the disparate track widths $W_A$, $W_C$, $W_D$ or adjustable to accommodate the disparate track widths $W_A$, $W_C$, $W_D$. Each of the gripper inverter conveyors 76A, 76C, 76D has a portion extending through the pre-wash station 44 as described in further detail below.

Figure 6:
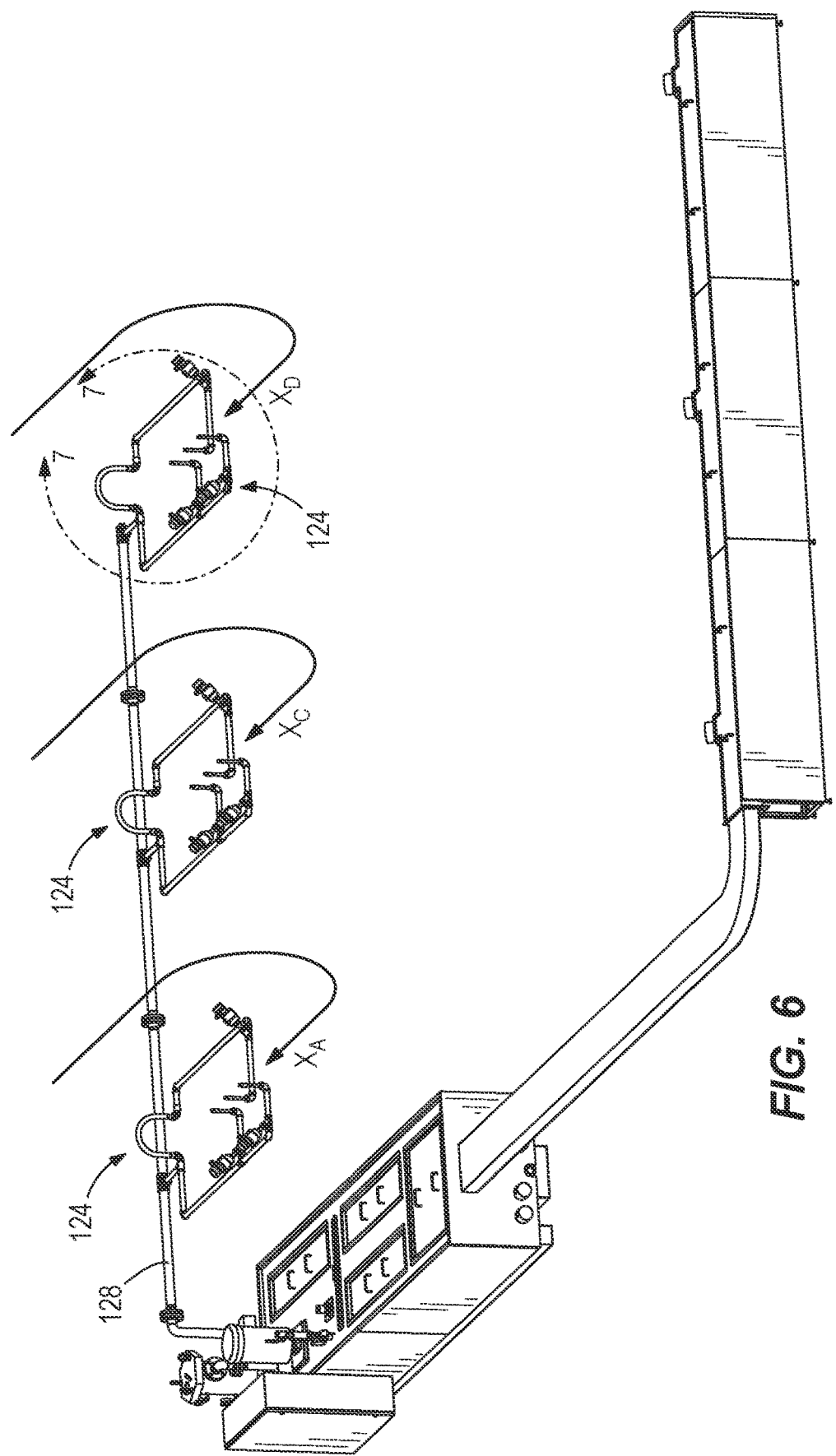
FIG. 6 is a perspective view of the pre-wash station isolated from the remainder of the medical waste disposal and container washing system. The pre-wash station is shown with three parallel wash stations.

As shown in the side elevation of FIG. 4, the first gripper inverter conveyor 76A defines a portion of the first conveyor lane 28A that makes a vertical U-turn or 180-degree change of direction defining a container path $X_A$ (see also FIG. 6). Although not separately shown, the other gripper inverter conveyors 76C, 76D and the manner in which they operate and interact within the system 20 can be the same as discussed herein with respect to the first gripper inverter conveyor 76A of FIG. 4. The path of the gripper inverter conveyor 76A enables it to operate by accepting containers C in a first or upright orientation (open top oriented upward) and gradually reorient the containers C to a second or inverted orientation (open top oriented downward) as they traverse an arcuate path. Exclusive of straight inlet and outlet portions, the path of the first gripper inverter conveyor 76A may form a semi-circle in some constructions. The gripper inverter conveyors 76A, 76C, 76D are integral segments of the respective conveyor lanes 28A, 28C, 28D. Thus, inverting the containers C with the gripper inverter conveyors 76A, 76C, 76D is configured to occur during operation and continuous movement of the conveyor system 28. The containers C do not stop, but rather are continuously moving along the conveyor system 28 during the act of dumping or emptying the containers C of their contents.

Entry to the gripper inverter conveyors 76A, 76C, 76D is provided by a height-adjustable portion of each conveyor lane 28A, 28C, 28D. The height adjustable portion is provided as a metering conveyor 80 (FIG. 4) positioned upstream of the inversion station 40 and configured to meter the transfer of containers C to the gripper inverter conveyor 76A. In the illustrated construction, an actuator 84 is operable to adjust a vertical position of an outlet or downstream end 80D of the metering conveyor 80 for setting a vertical position of an open top end of the container C being fed into the gripper inverter conveyor 76A. Via the controller 54, the vertical position of the top of the container C can be set to a predetermined height with respect to the inversion station 40, and the gripper inverter conveyor 76A in particular. The downstream end 80D of the metering conveyor 80 is shown in a raised position along with a phantom-line rendering of a lowered position in FIG. 4. The raised position can be utilized for a shorter container C, while the lowered position can be utilized for a taller container C (shown in phantom at left side of FIG. 4). The controller 54 can send an actuation signal to the actuator 84 (e.g., electric motor) based on a sensed vertical position of the container C obtained by a sensor 88 and reported from the sensor 88 to the controller 54. The sensor 88 can be an optical sensor, ultrasonic sensor, or another commercially available position detection device. The sensor 88, which may be referred to generally as a height sensor, can be positioned in an upstream portion of the metering conveyor 80 or upstream thereof.

Via the input from the sensor 88, and by way of the actuator 84, the controller 54 is configured to adjust the vertical position of the outlet end of the metering conveyor 80. To enable the adjustment, the metering conveyor 80 may be supported on a stationary conveyor frame 92 at a pivot 94 (e.g., a pivot pin, axle, etc. affording relative rotation about a horizontal axis). The actuator 84 can be coupled to the metering conveyor 80 via a mechanical link 96 (e.g., threaded rod, cable, rack-and-pinion, etc.) at a position further downstream from the pivot 94. For example, the mechanical link 96 can be connected to the metering conveyor 80 within a downstream half of the metering conveyor 80. Alternate structures for controlling vertical movement of the downstream end of the metering conveyor 80, whether through pivoting or other more complex kinematics, are also contemplated.

According to the preceding description, the metering conveyor 80 is operable to provide containers C to the gripper inverter conveyor 76A with a consistent, repeatable open end position regardless of the height dimension of the container C (i.e., containers having disparate heights). Thus, the gripper inverter conveyor 76A presents the containers C (the open ends thereof) at a consistent, repeatable position with respect to the pre-wash station 44 and also an adjacent downstream conveyor 100 that receives the pre-washed containers C from the gripper inverter conveyor 76A.

During reorientation by the gripper inverter conveyor 76A in the inversion station 40, some or all of the contents fall from the container C as illustrated symbolically by the arrow 104 in FIG. 4. The contents, which can include sharps and/or other medical waste products, fall by gravity from the container C onto a dewatering conveyor 108. As shown in FIG. 4, the primary receiving area of the dewatering conveyor 108 that receives some or all of the contents from the container C can be located nearer a downstream end 108D (right in FIG. 4) than an upstream end 108U (left in FIG. 4). Once the container C is inverted, it is transported by the gripper inverter conveyor 76A in a direction toward the upstream end 108U of the dewatering conveyor 108, at a position directly above the dewatering conveyor 108 so that remnant contents may also be received by the dewatering conveyor 108 from the container C following the initial or primary dumping. See for example, the end view of the inversion station 40 in FIG. 5, including all three gripper inverter conveyors 76A, 76C, 76D and their respective associated dewatering and downstream conveyors 108, 100. The downstream conveyor 100 receives the pre-washed containers C from the gripper inverter conveyor 76A and transports the containers C to the washer 52 of the second wash station 48.

The downstream portion of the gripper inverter conveyor 76A vertically overlaps with the pre-wash station 44 (shown schematically in FIG. 4) in such a way that the containers C are exposed to the pre-wash station 44. For example, the containers C may initially become exposed to the pre-wash station 44 during or at the point of completion of the reorientation to the inverted orientation. If exposed to the pre-wash station 44 before reorientation, the containers C continue to be exposed to the pre-wash station 44 following completion of the reorientation to the inverted orientation. The pre-wash station 44 is situated vertically at a height above the dewatering conveyor 108 and below the gripper inverter conveyor 76A. Contents from the containers C are carried to the downstream end 108D of the dewatering conveyor 108 and discharged therefrom as illustrated by arrow 112. The dewatering conveyor 108 can discharge onto an additional waste conveyor, or directly into a bin, shredder, incinerator, etc. As illustrated, the dewatering conveyor 108 is configured to discharge onto a separate waste conveyor or exit conveyor 116 (e.g., running transverse to the dewatering conveyor 108) that subsequently discharges the waste to a transfer bin 120 as shown in FIG. 1.

Figure 7:
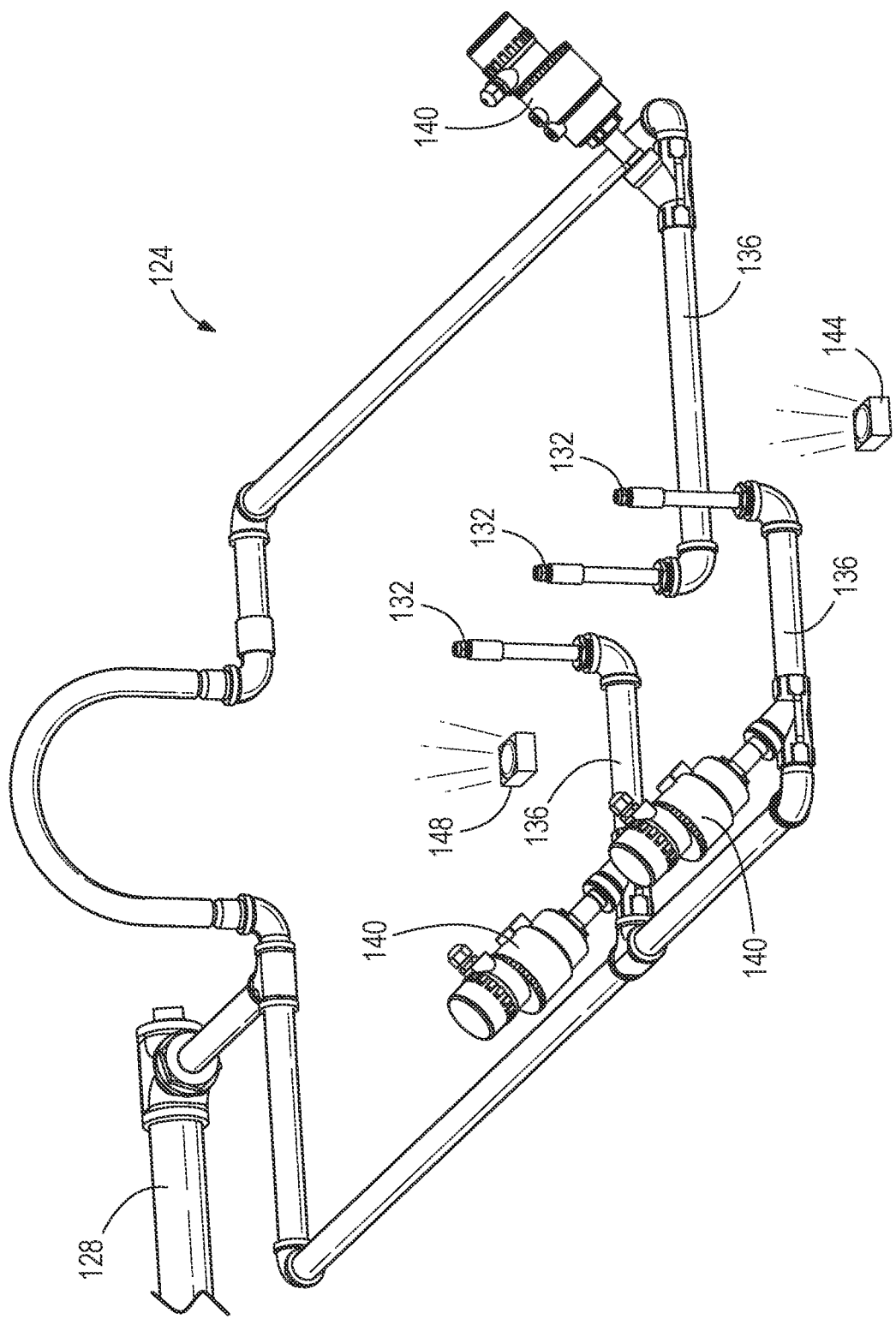
FIG. 7 is a detail view of one of the wash stations of the pre-wash station of FIG. 6.

Details of the pre-wash station 44 are described with particular reference to the embodiment illustrated in FIGS. 6 and 7. The pre-wash station 44 includes a number of wash stations 124, each wash station 124 configured to spray into the inverted containers C on one of the container conveyor lanes 28A, 28C, 28D. It bears repeating here that the system 20 as illustrated includes three container conveyor lanes 28A, 28C, 28D and three wash stations 124, but these may number greater or fewer than three in other constructions. The wash stations 124 are illustrated as having identical construction and being supplied from a common header or supply manifold 128. The respective container paths established by the three gripper inverter conveyors 76A, 76C, 76D are labeled $X_A$, $X_C$, $X_D$ in FIG. 6 for reference. Each wash station 124 includes one or more spray nozzles 132 configured to deliver a liquid spray (e.g., of water which can be heated water, with or without additive chemicals such as detergent(s) and/or cleaning chemicals) into the container C as the container, in the inverted orientation, is conveyed over the spray nozzle(s) 132. Although it will be appreciated that the liquid spray from the wash stations 124 can be water, a water-based solution, or another liquid, the below description simply refers to this as the liquid spray.

Thus, each spray nozzle 132 is located below the container's lowest point, which is the open end. The spray nozzles 132 in a given wash station 124 can all be identical, or they can be different. In some constructions, the spray nozzles 132 in a given wash station 124 all have the same orientation (e.g., vertical), while a wash station 124 of another construction may have spray nozzles 132 with different orientation(s). The spray nozzles 132 of a given wash station 124 are spaced apart along the respective container path $X_A$, $X_C$, $X_D$ through that wash station 124. In this way, the duration of the pre-washing action is not limited by the spray pattern of a single spray nozzle 132. The duration of the pre-wash into the container C may be 4 seconds or more (e.g., at least 5 seconds, or at least 6 seconds), despite running the containers along the conveyor system 28 at speeds over 10 feet per minute (e.g., at least 15 fpm, or at least 20 fpm).

Each of the spray nozzles 132 is in fluid communication with a supply of liquid for the liquid spray—via the supply manifold 128 in the illustrated construction—through a branch line 136 that can be selectively opened and closed. In some constructions, the branch lines 136 include electronically-controlled valves 140 operable to selectively open and close the respective branch lines 136 based upon the presence or absence of a container C. The valves 140 can take any number of physical forms to accomplish the opening and closing of the branch lines 136, resulting in the spray nozzles 132 selectively spraying the liquid and ceasing to spray water. The valves 140 can be controlled by the controller 54. In some embodiments, the controller 54 sends signals to the valves 140 to open and activate the spray nozzles 132 (sequentially or all at once) in response to detection of a container C just before the container C enters the wash station 124, (i.e., just before the container C reaches the upstream-most spray nozzle 132). Liquid sprayed from the nozzles 132 can drain through the dewatering conveyor 108 and route back to a holding tank so that it can be recirculated or repurposed.

The presence of the container C approaching the wash station 124 can be detected by a sensor 144 in communication with the controller 54. The sensor 144 can be an optical sensor, ultrasonic sensor, or another commercially available position detection device. Upon detection of the container C by the sensor 144 and corresponding activation of the spray nozzles 132, the controller 54 may control the duration of the liquid spray from the spray nozzles 132 so that they are deactivated (sequentially or all at once) just after the container C passes and is no longer in position to receive the liquid spray therefrom. The signal(s) to shut off the spray nozzles 132 in a given wash station 124 can be based on time duration (e.g., further based on a conveyor speed of the containers C through the pre-wash station 44) or active sensing by one or more additional downstream sensors 148 similar to the sensor 144 and operable to detect the position of the container C past the spray nozzle(s) 132.

With reference to the plan view of FIG. 1, the container conveyor lanes 28A, 28C, 28D can extend from the inversion unit 40 to transport the containers C (after the pre-wash station 44) along an "S"-shaped path to the washer 52. Meanwhile, in parallel, the lid conveyor lanes 28B, 28E can merge with the container conveyor lanes 28A, 28C, 28D. As shown, each of the lid conveyor lanes 28B, 28E can effectively define a U-turn path that reverses the overall direction of transport prior to reaching the washer 52. All lanes 28A-28E of the conveyor system 28 travel along parallel paths through the washer 52.

Figure 8:
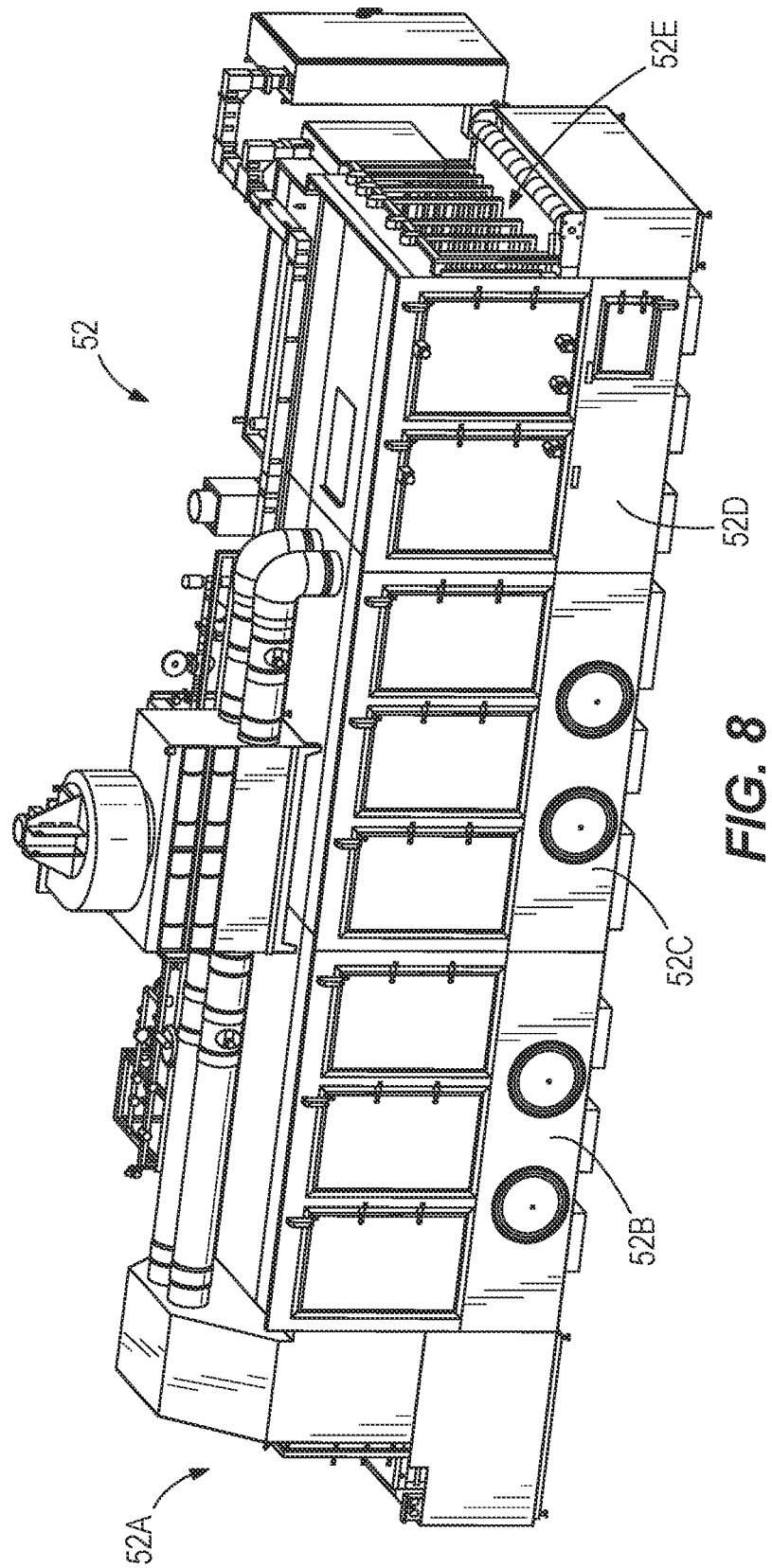
FIG. 8 is a perspective view of a tunnel washer of the medical waste disposal and container washing system of FIG. 1.

Turning to FIG. 8, an exemplary embodiment of the washer 52 providing the second wash station is shown. The washer has an inlet end 52A, a first or wash module 52B, a second or rinse module 52C, a third or drying module 52D, and an outlet end 52E. The washer 52 can disinfect, deodorize, and/or sanitize the containers C and lids L. Heated water in combination with additional optional detergents or cleaning chemicals are sprayed upon the containers C and the lids L within the washer 52, which is in the form of a tunnel open only at the inlet and outlet ends 52A, 52E. The conveyor system 28, which extends through the washer operates in some constructions to process at least 20 containers per minute through the washer 52 (e.g., and simultaneously the same rate of separated lids). In some constructions the conveyor system 28 operates to process at least 25 containers per minute (e.g., up to 30 containers per minute) through the washer 52. At the unloading station 32 at or downstream of the washer outlet end 52E, one or more workers can assemble the containers C with the appropriate lids L. The workers can package and/or load the containers C and lids L for transport out of the facility back into medical care facilities where they can be used again for sharps collection.

FDA certification of the system 20 may include the pre-wash station 44 as an integral portion of the system and process for processing of the sharps containers, which are considered medical devices by the FDA. Therefore, the washer 52 may not require its own certification, and the washer 52 is only jointly, and not solely, responsible for meeting the FDA certification for cleanliness and re-use of the containers C.

Although the invention has been described in detail with reference to certain preferred embodiments, variations and modifications exist within the scope and spirit of one or more independent aspects of the invention as described.

What is claimed is:

1. A medical waste disposal and container washing system comprising:
    a loading station located at an upstream end of the medical waste disposal and container washing system, wherein the loading station is configured for placing a medical waste container on a conveyor system;
    an inversion station located along the conveyor system downstream from the loading station and operable to reorient the medical waste container from a first orientation in which medical waste is retained within the medical waste container as the medical waste container is moved within the inversion station to a second orientation in which the medical waste is discharged from the medical waste container by gravity as the medical waste container is moved within the inversion station;
    a first wash station located along the conveyor system, wherein the first wash station is positioned and configured to wash an interior of the medical waste container that has been reoriented to the second orientation;
    a second wash station located along the conveyor system and downstream from the first wash station; and
    an unloading station downstream from the second wash station configured for removal of the medical waste container from the conveyor system, further comprising a dewatering conveyor positioned to receive medical waste discharged from the medical waster container as the medical waste container is moved within the inversion station, wherein the dewatering conveyor extends to the first wash station.

2. The medical waste disposal and container washing system of claim 1, further comprising a robotic tool located at the loading station and operable to disengage and remove a lid from the medical waste container.

3. The medical waste disposal and container washing system of claim 2, wherein the robotic tool is operable to place the lid removed from the container onto a chute that is configured to receive the removed lid and direct the lid onto a lid conveyor lane of the conveyor system for transport to the second washing station.

4. The medical waste disposal and container washing system of claim 1, wherein the conveyor system includes at least two conveyor lanes configured to receive respective medical waste containers, and wherein a first conveyor lane of the at least two conveyor lanes includes a first gripper inverter conveyor located in the inversion station, and a second conveyor lane of the at least two conveyor lanes includes a second gripper inverter conveyor located in the inversion station, wherein the first and second gripper inverter conveyors are operable to reorient the respective medical waste containers from the first orientation to the second orientation.

5. The medical waste disposal and container washing system of claim 4, wherein each of the first gripper inverter conveyor and the second gripper inverter conveyor has a portion extending through the first wash station.

6. The medical waste disposal and container washing system of claim 4, wherein the first gripper inverter conveyor has a first track width defined between opposed sets of grippers, and the first track width is different than a second track width defined between opposed sets of grippers of the second gripper inverter conveyor such that the first gripper inverter conveyor and second gripper inverter conveyor are configured to grip medical waste containers of disparate sizes.

7. The medical waste disposal and container washing system of claim 1, wherein the first wash station includes one or more spray nozzles configured to deliver fluid into the medical waste container when the medical waste container has been reoriented to the second orientation.

8. The medical waste disposal and container washing system of claim 7, wherein the one or more spray nozzles includes a plurality of spray nozzles spaced along a travel direction of the conveyor system along which the medical waste container is transported through the first wash station, and wherein the plurality of spray nozzles is located below the medical waste container reoriented to the second orientation.

9. The medical waste disposal and container washing system of claim 1, wherein the conveyor system includes at least two conveyor lanes configured to receive respective medical waste containers, wherein a first conveyor lane of the at least two conveyor lanes includes a first gripper inverter conveyor located in the inversion station and a first set of spray nozzles of the first wash station, and a second conveyor lane of the at least two conveyor lanes includes a second gripper inverter conveyor located in the inversion station and a second set of spray nozzles of the first wash station, wherein the first gripper inverter conveyor and second gripper inverter conveyor are operable to reorient the respective medical waste containers from the first orientation to the second orientation, and wherein the first and second sets of spray nozzles are configured for independent operation.

10. The medical waste disposal and container washing system of claim 1, further comprising:
 a medical waste collection station including at least one waste collection bin positioned remote from the inversion station; and
 an exit conveyor configured to receive medical waste from the dewatering conveyor, the exit conveyor extending from the dewatering conveyor to the waste collection bin.

11. The medical waste disposal and container washing system of claim 1, wherein the dewatering conveyor is a first dewatering conveyor configured to receive medical waste from a first medical waste container engaged by a first gripper inverter conveyor of the inversion station, further comprising a second dewatering conveyor configured to receive medical waste from a second medical waste container engaged by a second gripper inverter conveyor of the inversion station.

12. The medical waste disposal and container washing system of claim 1, further comprising a controller and a medical waste container sensor coupled to the controller, wherein the medical waste container sensor is positioned along the conveyor system and operable to detect the presence of the medical waste container, and in response to receiving a signal from the medical waste container indicating the presence of the medical waste container, the controller is configured to activate a spray nozzle located in the first wash station.

13. The medical waste disposal and container washing system of claim 1, wherein the conveyor system includes multiple lanes extending to an inlet of the second wash station including at least two lanes configured to transport medical waste containers, each lane of the at least two lanes configured to transport medical waste containers from one of at least two gripper inverter conveyors of the inversion station, and at least one lane of the multiple lanes configured to transport medical waste container lids to the second wash station, wherein the at least one lane configured to transport medical waste container lids bypasses the first wash station.

14. The medical waste disposal and container washing system of claim 1, wherein the conveyor system is configured to move the medical waste container continuously through the inversion station, from the inversion station to the first wash station, through the first wash station, from the first wash station to the second wash station, and through the second wash station without stopping.

15. A medical waste disposal and container washing system comprising: a loading station located at an upstream end of the medical waste disposal and container washing system, wherein the loading station is configured for placing a medical waste container on a conveyor system; an inversion station located along the conveyor system downstream from the loading station and operable to reorient the medical waste container from a first orientation in which medical waste is retained within the medical waste container as the medical waste container is moved within the inversion station to a second orientation in which the medical waste is discharged from the medical waste container by gravityas the medical waste container is moved within the inversion station; a first wash station located along the conveyor system, wherein the first wash station is positioned and configured to wash an interior of the medical waste container that has been reoriented to the second orientation; a second wash station located along the conveyor system and downstream from the first wash station; and an unloading station downstream from the second wash station configured for removal of the medical waste container from the conveyor system,
 wherein the conveyor system includes at least two conveyor lanes configured to receive respective medical waste containers, and wherein a first conveyor lane of the at least twoconveyor lanes includes a first gripper inverter conveyor located in the inversion station, and a second conveyor lane of the at least two conveyor lanes includes a second gripper inverter conveyor located in the inversion station, wherein the first and second gripper inverter conveyors are operable to reorient the respective medical waste containers from the first orientation to the second orientation,
 wherein the first gripper inverter conveyor has a first track width defined between opposed sets of grippers, and the first track width is different than a second track width defined between opposed sets of grippers of the second gripper inverter conveyor such that the first gripper inverter conveyor and second gripper inverter conveyor are configured to grip medical waste containers of disparate sizes.

* * * * *

UNITED STATES PATENT AND TRADEMARK OFFICE
CERTIFICATE OF CORRECTION

| | | |
|---|---|---|
| PATENT NO. | : 12,161,852 B2 | Page 1 of 1 |
| APPLICATION NO. | : 17/744427 | |
| DATED | : December 10, 2024 | |
| INVENTOR(S) | : Matthew S. LaTorre et al. | |

It is certified that error appears in the above-identified patent and that said Letters Patent is hereby corrected as shown below:

In the Claims

Column 11 Claim 1, Line 66: please replace "medical waster container" with --medical waste container--

Column 14 Claim 15, Line 14: please replace "gravityas" with --gravity as--

Column 14 Claim 15, Line 28: please replace "twoconveyor" with --two conveyor--

Signed and Sealed this
Fifteenth Day of April, 2025

Coke Morgan Stewart
*Acting Director of the United States Patent and Trademark Office*